US008642580B2

(12) United States Patent
Geroni et al.

(10) Patent No.: US 8,642,580 B2
(45) Date of Patent: *Feb. 4, 2014

(54) COMBINED THERAPY AGAINST TUMORS COMPRISING SUBSTITUTED ACRYLOYL DISTAMYCIN DERIVATIVES AND PLATINUM DERIVATIVES

(75) Inventors: M. Cristina Geroni, Milan (IT); Paolo Cozzi, Milan (IT); Italo Beria, Nerviano-Milan (IT)

(73) Assignee: Nerviano Medical Sciences S.R.L., Nerviano Milan (IT)

( * ) Notice: Subject to any disclaimer, the term of this patent is extended or adjusted under 35 U.S.C. 154(b) by 132 days.

This patent is subject to a terminal disclaimer.

(21) Appl. No.: 10/311,995

(22) PCT Filed: Jun. 20, 2001

(86) PCT No.: PCT/EP01/07064
§ 371 (c)(1),
(2), (4) Date: Dec. 23, 2002

(87) PCT Pub. No.: WO01/97790
PCT Pub. Date: Dec. 27, 2001

(65) Prior Publication Data
US 2003/0180383 A1    Sep. 25, 2003

(30) Foreign Application Priority Data

Jun. 23, 2000  (GB) .................. 0015447.6

(51) Int. Cl.
*A01N 43/00* (2006.01)
*A61K 31/33* (2006.01)
*A61K 38/00* (2006.01)
*A61P 35/00* (2006.01)
*A61P 35/02* (2006.01)

(52) U.S. Cl.
USPC ........ 514/183; 514/19.2; 514/19.3; 514/19.4; 514/19.6

(58) Field of Classification Search
USPC ......... 514/18, 428, 422, 408, 183, 19.2, 19.3, 514/19.4, 19.6
See application file for complete search history.

(56) References Cited

U.S. PATENT DOCUMENTS

| 4,359,425 A | * | 11/1982 | Totani et al. .................. 556/137 |
| 5,646,177 A | | 7/1997 | Koch et al. |
| 5,880,097 A | | 3/1999 | Lyttle et al. |

FOREIGN PATENT DOCUMENTS

| EP | 0 246 868 | 11/1987 |
| EP | 0 265 719 | 5/1988 |
| EP | 0 388 948 | 9/1990 |
| EP | 0 420 121 | 4/1991 |
| GB | 2 178 036 | 2/1987 |
| WO | WO 90 11277 A | 10/1990 |
| WO | WO 96 05196 A | 2/1996 |
| WO | WO 97 28123 | 8/1997 |
| WO | WO 97 43258 | 11/1997 |
| WO | WO 98 04524 A | 2/1998 |
| WO | WO 98/04524 | * 5/1998 |
| WO | WO 98 21202 A | 5/1998 |
| WO | WO 99/34796 | * 7/1999 |
| WO | WO 99 34796 A | 7/1999 |
| WO | WO 99 50265 A | 10/1999 |
| WO | WO 99 50266 | 10/1999 |
| WO | WO 99/50266 | * 10/1999 |
| WO | WO 99 50266 A | 10/1999 |
| WO | WO 00 06541 | 2/2000 |
| WO | WO 00 06542 | 2/2000 |
| WO | WO 01 40181 A | 6/2001 |
| WO | WO 01 85144 | 11/2001 |

OTHER PUBLICATIONS

Remington's Pharmaceutical Sciences, 16th edition, 1980, Mack Publishing Co., pp. 420-435.*
Drug Facts and Comparisons, 1994 edition, Wolters Kluwer Co., pp. 2637-2639.*
Cecil's Textbook of Medicine (2000).*
Schoffski et al. (Annals of Oncology, 1999, 119-122).*
Sola F et al: "The antitumor efficacy of cytotoxic drugs is potentiated by growth-factor-complexing molecule" Cancer Chemotherapy and Pharmacology, vol. 43, No. 3, 1999, pp. 241-246, XP002104215. ISSN: 0344-5704.
Zou J P et al: "Distamycin A derivatives potentiate tumor-necrosis factor activity via the modulation of tyrosine phosphorylation" International Journal Fo Cance, New York, NY, US, vol. 72, No. 5, 1997, pp. 810-814, XP002104217 ISSN: 0020-7136.
Tsuchida S et al: "Elevation of the Placental Glutathione-S-Transferase Form GST-PI in Tumor Tissues and the Levels in Sera of Patients With Cancer" Cancer Research, vol. 49, No. 18, 1989, pp. 5225-5229, XP001039783 ISSN: 0008-5472 abstract p. 5225, column 1, paragraph 1, p. 5228, col. 1, paragraph 1 p. 5228, col. 2. paragraph 2.
Catharina J A Van Moorsel et al: XP002110339 "Gemcitabine: Futrue Prospects of Single-Agent and Combination Studies" Oncologist, Alphamed Press, US, vol. 2, No. 3, 1997, pp. 127-134, ISSN: 1083-7159.
Colella, G. et al: "Mismatch repair deficiency is associated with resistance to DNA minor groove alkylating agents" Br. J. Cancer (1999), 80(3/4), 338-343, XP001039733.
Giusti Anna Maria et al: "In vivo induction of apoptosis with PNU-166196 in human ovarian carcinoma xenografts." Proceedings of the American Association for Cancer Research Annual, No. 41, Mar. 2000, p. 825 XP001039865 91st Annual Meeting of the American Association for Cancer Research.: San Francisco, California, USA; Apr. 1-5, 2000, Mar. 2000 ISSN: 0197-016X.

(Continued)

Primary Examiner — Sreeni Padmanabhan
Assistant Examiner — Uma Ramachandran
(74) Attorney, Agent, or Firm — Scully, Scott, Murphy & Presser, P.C.

(57) ABSTRACT

Compounds which are α-halogenoacryloyl distamycin derivatives of formula (I) wherein $R_1$ is a bromine or chlorine atom; $R_2$ is a distamycin or distamycin-like framework as set forth in the specification; or a pharmaceutically acceptable salt thereof; are cytotoxic agents particularly effective in the treatment of tumors over expressing GSH/GSTs system and which are poorly responsive or even resistant to conventional antitumor therapies.

7 Claims, No Drawings

(56) References Cited

OTHER PUBLICATIONS

Budavari S (Ed): XP002191966 "The Merck Index (12th Edition)" Merck Index, Encyclopedia of Chemicals, Drugs, and Biologicals, 13th. Edition 1996, Whitehouse Station, Merck & Co, US, vol. ED. 13, 2001, p. 4206 ISBN: 0-911910-12-3.
Cozzi P: "A new class of cytotoxic DNA minor groove binders: alpha-halogenoacrylic derivatives of pyrrolecarbamoyl oligomers." Farmaco,(Jan.-Feb.2001) 56 (1-2) 57-65., XP001039805 abstract p. 58, col. 2, paragraph 4 p. 59, col. 1, paragraph 1 figure 5 p. 60, col. 1, paragraph 2-p. 61, col. 1, paragraph 4 tables 2,3 p. 62, col. 2, paragraph 3 figures 9, 10 table 5 p. 63, col. 1, paragraph 1-col. 2, paragraph 2.
Baraldi, Pier Giovanni et al: "Synthesis and Antitumor Activity of New Benzoheterocyclic Derivatives of Distamycin A" J. Med. Chem. (2000), 43(14), 2675-2684 , Jul. 13, 2000, XP001039581 abstract p. 2676, col. 1; tables p. 2676, col. 1, paragraph 1 tables 1,2 p. 2678, col. 2, paragraph 5 -p. 2679, col. 1, paragraph1 p. 2680, col. 2, paragraph 3.
Mosconi A M et al: XP004282426 "Combination Therapy with Gemcitabine in Non-small Cell Lung Cancer" European Journal of Cancer, Pergamon Press, Oxford, GB, vol. 33, Jan. 1997, pp. S14-S17, ISSN: 0959-8049.
D'Alessio, Roberto et al: "Structure-activity relationship of novel distamycin A derivatives: Synthesis and antitumor activity" Bioorg. Med. Chem. Lett. (1994), 4(12), 1467-72, XP000671766.
Geroni Cristina et al: "Antitumor activity of PNU-166196, a novel DNA minor groove binder selected for clinical development." Proceedings of the American Association for Cancer Research Annual, No. 41, Mar. 2000, pp. 425-426, XP001039861 91st Annual Meeting of the American Association for Cancer Research.; San 2000, Mar. 2000 ISSN: 0197-016X.
Stewart D J et al: "Non-Chemotherapeutic Agents That Potentiate Chemotherapy Efficacy" Cancer Treatment Reviews, vol. 16, No. 1, 1989, pp. 1-40, XP001039737 ISSN: 0305-7372 p. 18, paragraph 3-p. 19, paragraph 1.
Baraldi, Pier Giovanni et al: "Synthesis and antitumor activity of novel distamycin derivatives" Bioorg. Med. Chem. Lett. (1996), 6(11), 1241-1246 XP004134862 p. 1241, paragraph 2 example SCHEME1 p. 1244, paragraph 1 table 1 p. 1244, paragraph 4-p. 1245, paragraph 1.
Geroni C et al: "PNU-166196: A novel antitumor agent whose cytotoxicity is enhanced in tumor cells with high levels of glutathione." TUMORI, vol. 86, No. 4 Suppl. 1, Jul. 2000, pp. 41-42, XP001039871 XV Congress of the Italian Cancer Society; Turin, Italy; Oct. 5-7, 2000 ISSN: 0300-8916.
Boger et al., "Total Synthesis of Distamycin A and 2640 Analogues: A Solution-Phase Combinatorial Approach to the Discovery of New Bioactive DNA Binding Agents and Development of a Rapid, High-Throughput Screen for Determining Relative DNA Binding Affinity or DNA Binding Sequence Selectivity", J. Am. Chem. Soc. 2000, 122, 6382-6394.
Tagliabue G., et al., "Combination of the New Minor Groove Alkylator Tallimustine and Melphalan", Wuropean Journal of Cancer, Pergamon Press, Oxford, GB, vol. 33, No. 2, Feb. 1997, pp. 284-287.
Cozzi P., et al., "Cytotoxic alpha-bromoacrylic derivatives of distamycin analogues modified at the amidino moiety" Bioorganic & Medicinal Chemistry Letters, Oxford, GB, vol. 10, No. 11, Jun. 2000, pp. 1273-1276.
Cozzi P., et al., "Cytotoxic halogenoacrylic derivatives of distamycin A", Bioorganic & Medicinal Chemistry Letters, Oxford, GB, vol. 10, No. 11, Jun. 2000, pp. 1269-1272.

* cited by examiner

COMBINED THERAPY AGAINST TUMORS COMPRISING SUBSTITUTED ACRYLOYL DISTAMYCIN DERIVATIVES AND PLATINUM DERIVATIVES

CROSS-REFERENCE TO RELATED APPLICATION

This application is a National Stage entry of International Application No. PCT/EP01/07064, filed Jun. 20, 2001, the entire specification claims and drawings of which are incorporated herewith by reference.

The present invention relates to the field of cancer treatment and provides an antitumor composition comprising a substituted acryloyl distamycin derivative, more particularly an α-bromo- or α-chloro-acryloyl distamycin derivative, and an alkylating agent, having a synergistic antineoplastic effect.

Distamycin A and analogues thereof; hereinafter referred to as distamycin and distamycin-like derivatives, are known in the art as cytotoxic agents useful in antitumor therapy.

Distamycin A is an antibiotic substance with antiviral and antiprotozoal activity, having a polypyrrole framework [Nature 203: 1064 (1964); *J. Med. Chem.* 32: 774-778 (1989)]. The international patent applications WO 90/11277, WO 98/04524, WO 98/21202, WO 99/50265, WO 99/50266 and WO 01/40181 (claiming priority from British patent application No. 9928703.9), all in the name of the applicant itself and herewith incorporated by reference, disclose acryloyl distamycin derivatives wherein the amidino moiety of distamycin is optionally replaced by nitrogen-containing ending groups such as, for instance, cyanamidino, N-methylamidino, guanidino, carbamoyl, amidoxime, cyano and the like, and/or wherein the polypyrrole framework of distamycin, or part of it, is replaced by varying carbocyclic or heterocyclic moieties.

The present invention provides, in a first aspect, a pharmaceutical composition for use in antineoplastic therapy in mammals, including humans, comprising a pharmaceutically acceptable carrier or excipient;
an acryloyl distamycin derivative of formula (I):

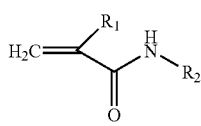

(I)

wherein:
$R_1$ is a bromine or chlorine atom;
$R_2$ is a distamycin or distamycin-like framework; or a pharmaceutically acceptable salt thereof, and
an alkylating agent.

The present invention includes, within its scope, the pharmaceutical compositions comprising any of the possible isomers covered by the compounds of formula (I), both considered separately or in admixture, as well as the metabolites and the pharmaceutically acceptable bio-precursors (otherwise known as pro-drugs) of the compounds of formula (I).

In the present description, unless otherwise specified, with the term distamycin or distamycin-like framework $R_2$ we intend any moiety structurally closely related to distamycin itself, for instance by optionally replacing the ending amidino moiety of distamycin and/or its polypyrrole framework, or part of it.

Alkylating agents are widely known in the art as described in various scientific publications.

Representatives for this class of compounds are, for instance, mustards such as melphalan, chlorambucil, mechlorethamine, cyclophosphamide, ifosfamide and busulfan; nitrosoureas such as carmustine, lormustine, semustine and fotemustine; tetrazines such as dacarbazine and temozolomide; aziridines such as thiotepa and mitomycin C and platinum derivatives such as cisplatin, carboplatin, oxaliplatin, nedaplatin and lobaplatin and the like.

See, for a general reference, Cancer Principles and Practice of Oncology, Lippincott-Raven Ed. (1997), 405-432.

According to a preferred embodiment of the invention, herewith provided are the above pharmaceutical compositions wherein the alkylating agent is selected from mustards and platinum derivatives such as cisplatin, carboplatin and oxaliplatin.

According to another preferred embodiment of the invention, herewith provided are the above pharmaceutical compositions wherein, within the acryloyl distamycin derivative of formula (I), $R_1$ has the above reported meanings and $R_2$ is a group of formula (II) below:

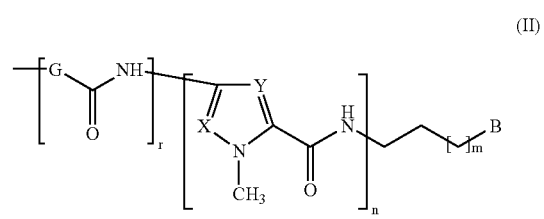

(II)

wherein
m is an integer from 0 to 2;
n is an integer from 2 to 5;
r is 0 or 1;
X and Y are, the same or different and independently for each heterocyclic ring, a nitrogen atom or a CH group;
G is phenylene, a 5 or 6 membered saturated or unsaturated heterocyclic ring with from 1 to 3 heteroatoms selected among N, O or S, or it is a group of formula (III) below:

(III)

wherein Q is a nitrogen atom or a CH group and W is an oxygen or sulfur atom or it is a group $NR_3$ wherein $R_3$ is hydrogen or $C_1$-$C_4$ alkyl;
B is selected from the group consisting of

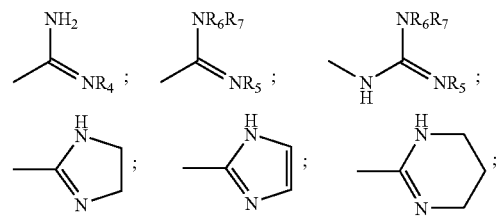

—CN; —$NR_5R_6$; —$CONR_5R_6$; —$NHCONR_5R_6$ wherein $R_4$ is cyano, amino, hydroxy or $C_1$-$C_4$ alkoxy; $R_5$, $R_6$ and $R_7$, the same or different, are hydrogen or $C_1$-$C_4$ alkyl.

In the present description, unless otherwise specified, with the term $C_1$-$C_4$ alkyl or alkoxy group we intend a straight or branched group selected from methyl, ethyl, n-propyl, isopropyl n-butyl, isobutyl, sec-butyl, tert-butyl, methoxy, ethoxy, n-propoxy, isopropoxy, n-butoxy, isobutoxy, sec-butoxy or tert-butoxy.

Even more preferred are the pharmaceutical compositions of the invention comprising the above acryloyl distamycin derivative of formula (I) wherein $R_1$ is bromine or chlorine; $R_2$ is the above group of formula (II) wherein r is 0, m is 0 or 1, n is 4 and B has the above reported meanings.

Still more preferred, within this class, are the pharmaceutical compositions comprising the compounds of formula (I) wherein $R_1$ is bromine or chlorine; $R_2$ is the above group of formula (II) wherein r is 0, m is 0 or 1, n is 4, X and Y are both CH groups and B is selected from:

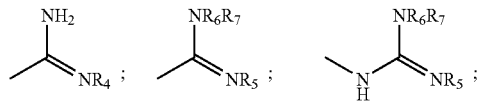

—CN; —CONR$_5$R$_6$; —NHCONR$_5$R$_6$
wherein $R_4$ is cyano or hydroxy and $R_5$, $R_6$ and $R_7$, the same or different, are hydrogen or $C_1$-$C_4$ alkyl.

Pharmaceutically acceptable salts of the compounds of formula (I) are those with pharmaceutically acceptable inorganic or organic acids such as, for instance, hydrochloric, hydrobromic, sulfuric, nitric, acetic, propionic, succinic, malonic, citric, tartaric, methanesulfonic, p-toluenesulfonic acid and the like.

Examples of preferred acryloyl distamycin derivatives of formula (I), within the compositions object of the invention, optionally in the form of pharmaceutically acceptable salts, preferably with hydrochloric acid, are:
1. N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;
2. N-(5-{[(5-{[(5-{[(2-{[amino(imino)methyl]amino}propyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;
3. N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)4-[(2-bromoacryloyl)amino]-1-methyl-1H-pyrrole-2-carboxamide hydrochloride;
4. N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-imidazole-2-carboxamide hydrochloride;
5. N-(5-{[(5-{[(5-{[(3-amino-3-iminopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide hydrochloride;
6. N-(5-{[(5-{[(5-{[(3-amino-3-oxopropyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-3-[(2-bromoacryloyl)amino]-1-methyl-1H-pyrazole-5-carboxamide;
7. N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)4-[(2-chloroacryloyl)amino]-1-methyl-1H-pyrrole-2-carboxamide hydrochloride;
8. N-(5-{[(5-{[(3-{[amino(imino)methyl]amino}propyl)amino]carbonyl}-1-methyl-1H-pyrrol-3-yl)amino]carbonyl}-1-methyl-1H-pyrrol-3-yl)4-[(2-bromoacryloyl)amino]-1-methyl-1H-pyrrole-2-carboxamide hydrochloride;
9. N-(5-{[(5-{[(3-amino-3-iminopropyl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride; and
10. N-{5-[({5-[({5-[({3-[(aminocarbonyl)amino]propyl}amino)carbonyl]-1-methyl-1H-pyrrol-3-yl}amino)carbonyl]-1-methyl-1H-pyrrol-3-yl}amino)carbonyl]-1-methyl-1H-pyrrol-3-yl}-4-[(2-bromoacryloyl)amino]-1-methyl-1H-pyrrole-2-carboxamide.

The above compounds of formula (I), either specifically identified as such or by means of the general formula, are known or easily prepared according to known methods as reported, for instance, in the aforementioned international patent applications WO 90/11277, WO 98/04524, WO 98/21202, WO 99/50265 and WO 99/50266 as well as in WO 01/40181.

The present invention further provides a product comprising an acryloyl distamycin derivative of formula (I), as defined above, and an alkylating agent, as a combined preparation for simultaneous, separate or sequential use in antitumor therapy.

A further aspect of the present invention is to provide a method of treating a mammal, including humans, suffering from a neoplastic disease state, which method comprises administering to said mammal the above acryloyl distamycin derivative of formula (I) and an alkylating agent, in amounts effective to produce a synergistic antineoplastic effect.

The present invention also provides a method for lowering the side effects caused by antineoplastic therapy with an antineoplastic agent in a mammal in need thereof, including humans, the method comprising administering to said mammal a combined preparation comprising an alkylating agent and an acryloyl distamycin derivative of formula (I), as defined above, in amounts effective to produce a synergistic antineoplastic effect.

By the term "synergistic antineoplastic effect", as used herein, it is meant the inhibition of the growth tumor, preferably the complete regression of the tumor, by administering an effective amount of the combination comprising an acryloyl distamycin derivative of formula (I) and an alkylating agent to mammals, including humans.

By the term "administered" or "administering", as used herein, it is meant parenteral and/or oral administration; the term "parenteral" means intravenous, subcutaneous and intramuscular administration.

In the method of the present invention, the acryloyl distamycin derivative may be administered simultaneously with the alkylating agent or, alternatively, both compounds may be administered sequentially in either order.

In this respect, it will be appreciated that the actual preferred method and order of administration will vary according to, inter alia, the particular formulation of the acryloyl distamycin of formula (I) being used, the particular formulation of the alkylating agent being used, the particular tumor model being treated as well as the particular host being treated.

To administer the acryloyl distamycin derivative of formula (I), according to the method of the invention, the course of therapy generally employed comprises doses varying from about 0.05 to about 100 mg/m² of body surface area and, more preferably, from about 0.1 to about 50 mg/m² of body surface area.

For the administration of the alkylating agent, according to the method of the invention, the course of therapy generally employed comprises:

for the administration of mustard compounds doses varying from about 1 mg/m² to about 5000 mg/m² of body surface area and, more preferably, from about 10 to about 1000 mg/m² of body surface area.

for the administration of nitrosourea derivatives doses varying from about 1 mg/m² to about 1000 mg/m² of body surface area and, more preferably, from about 10 to about 1000 mg/m² of body surface area.

for the administration of tetrazine and aziridine compounds doses varying from about 1 mg/m² to about 1000 mg/m² of body surface area and, more preferably, from about 10 to about 1000 mg/m² of body surface area.

for the administration of platinum derivatives doses varying from about 1 mg/m² to about 1000 mg/m² of body surface area and, more preferably, from about 10 to about 500 mg/m² of body surface area.

The antineoplastic therapy of the present invention is particularly suitable for treating breast, ovary, lung, colon, kidney, stomach, pancreas, liver, melanoma, leukemia and brain tumors in mammals, including humans.

In a further aspect, the present invention is directed to the preparation of a pharmaceutical composition comprising an effective amount of an acryloyl distamycin derivative of formula (I), as defined above, and an alkylating agent, in the preparation of a medicament for use in the prevention or treatment of metastasis or in the treatment of tumors by inhibition of angiogenesis.

As stated above, the effect of an acryloyl distamycin derivative of formula (I) and an alkylating agent, for instance cisplatin and carboplatin, is significantly increased without a parallel increase of toxicity. In other words, the combined therapy of the present invention enhances the antitumoral effects of the acryloyl distamycin derivative and of the alkylating agent and, hence, provides the most effective and least toxic treatment for tumors.

The synergistic or superadditive effect of the combined preparations of the invention is shown, for instance, by the following in vivo tests which are intended to illustrate the present invention without posing any limitation to it.

Table 1 shows the antileukemic activity on disseminated L1210 murine leukemia obtained by combining the representative compound of formula (I) of the invention N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride—internal code PNU 166196, with cisplatin.

At the dose of 5.9 mg/kg of cisplatin alone (day +3) and at the dose of 0.26 mg/kg of PNU 166196 alone (days +1,2) were associated, without toxicity, with ILS % values of 67 and 33, respectively.

Combining cisplatin and PNU 166196 at the same doses with the same schedule, an increase of activity with ILS % values of 125 were observed, thus indicating a synergistic antitumor effect.

Table 2 shows the antileukemic activity on disseminated L1210 murine leukemia obtained by combining the above PNU 166196 derivative with carboplatin.

At the dose of 135 mg/kg of carboplatin alone (day +3) and at the dose of 0.26 mg/kg of PNU 166196 alone (days +1,2) were associated, without toxicity, with ILS % values of 50 and 33, respectively.

By combining carboplatin and PNU 166196 at the same doses and with the same schedule, an increase of activity with ILS % values of 92 were observed, again indicating a more than additive effect.

Table 3 shows the antitumor effect on subcutaneous implanted HCT-116 human colon carcinoma obtained by combining PNU 166196 with cisplatin.

At the dose of 2 mg/kg of cisplatin alone (q7dx3) and at the dose of 0.4 mg/kg of PNU 166196 alone (q7dx3) were associated, without toxicity, T/C % values of 92 and 61, respectively.

By combining cisplatin and PNU 166196, instead, a significant increase in tumor growth delay was observed, hence indicating a therapeutic advantage of the combination (synergism) in comparison to the administration of the drugs alone.

For these experiments PNU 166196 was solubilized in water for injection, while standard pharmaceutical preparations were used for cisplatin and carboplatin.

TABLE 1

Antileukemic activity against disseminated L1210[1] murine leukemia of an acryloyl distamycin derivative (I) in combination with cisplatin.

| Compound | Treatment[2] schedule | Dose (mg/kg/day) | ILS %[3] | Tox[4] |
|---|---|---|---|---|
| PNU 166196 | iv +1, 2 | 0.26 | 33 | 0/10 |
| Cisplatin | iv +3 | 5.9 | 67 | 0/10 |
| PNU 166196 + Cisplatin | iv +1, 2 iv +3 | 0.26 + 5.9 | 120 | 0/10 |

[1]L1210 leukemia cells (10⁵/mouse CD2F1) are injected IV on Day 0.
[2]Treatment is given IV.
[3]Increase in life span: [(median survival time of treated mice/median survival time of controls) × 100] − 100.
[4]Number of toxic deaths/number of mice.

TABLE 2

Antileukemic activity against disseminated L1210[1] murine leukemia of an acryloyl distamycin derivative in combination with carboplatin.

| Compound | Treatment schedule | Dose[2] (mg/kg/day) | ILS %[3] | Tox[4] |
|---|---|---|---|---|
| PNU-166196 | iv +1, 2 | 0.26 | 33 | 0/10 |
| Carboplatin | iv +3 | 135 | 50 | 0/10 |
| PNU-166196 + Carboplatin | iv +1, 2 iv +3 | 0.26 + 435 | 92 | 0/10 |

[1]L1210 leukemia cells (10⁵/mouse CD2F1) are injected IV on Day 0.
[2]Treatment is given IV.
[3]Increase in life span: [(median survival time of treated mice/median survival time of controls) × 100] − 100.
[4]Number of toxic deaths/number of mice.

TABLE 3

Antitumor activity against human colon carcinoma HCT-116 (low/medium GST and MMR deficiency) of an acryloyl distamycin derivative in combination with cisplatin.

| Compound | Dose[a] (mg/kg) | T/C %[b] | Log cell Kill total | Tumor free/total mice[c] | WL % (day of nadir)[d] |
|---|---|---|---|---|---|
| PNU-166196 | 0.4 | 61 | 0.15 | 0/8 | 12 (29) |
| Cisplatin | 2 | 92 | 0 | 0/7 | 12 (24) |
| PNU-166196 + Cisplatin | 0.4 + 2 | 36 (synergic)[e] | 0.7 | 1/7 | 13 (27) |

[a]Treatment IV started on day 7 after tumor implant; schedule q7dx3 of PNU 166196 administered 48 hours after cisplatin;
[b]Tumor regression (T/C %) on day 20 after treatment (according to NCI standards: T/C ≤ 42 active);
[c]On day 40 after tumor implant;
[d]27 days after tumor implant;
[e]Fisher's test vs. both cisplatin and PNU 166196

The invention claimed is:

1. A method of treating a mammal suffering from a neoplastic disease state, the neoplastic disease state selected from the group consisting of colon cancer and leukemia, which method comprises administering to said mammal an acryloyl distamycin derivative, N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride, optionally in the form of a pharmaceutically acceptable salt, at a concentration of about 0.26 mg/kg/day to about 0.4 mg/kg/day;

and cisplatin at a concentration of about 2.0 mg/kg/day to about 5.9 mg/kg/day, in amounts effective to produce a synergistic antineoplastic effect.

2. The method according to claim 1 wherein the mammal is a human.

3. A method of treating a mammal suffering from a neoplastic disease, the neoplastic disease selected from the group consisting of colon cancer and leukemia, the method comprising administering to said mammal brostallicin or a pharmaceutically acceptable salt thereof at a concentration of about 0.26 mg/kg/day to about 0.4 mg/kg/day, and cisplatin at a concentration of about 2.0 mg/kg/day to about 5.9 mg/kg/day, wherein said brostallicin is an acryloyl distamycin derivative corresponding to the following name:

N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;

wherein said brostallicin and cisplatin are administered in amounts effective to produce a synergistic antineoplastic effect.

4. A method for lowering the side effect of weight loss in a mammal suffering from a neoplastic disease, the neoplastic disease selected from the group consisting of colon cancer and leukemia, and undergoing antineoplastic therapy, the method comprising administering to a mammal undergoing antineoplastic therapy brostallicin or a pharmaceutically acceptable salt thereof at a concentration of about 0.26 mg/kg/day to about 0.4 mg/kg/day, and cisplatin at a concentration of about 2.0 mg/kg/day to about 5.9 mg/kg/day, wherein said brostallicin is an acryloyl distamycin derivative corresponding to the following name:

N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride;

wherein said brostallicin and cisplatin are administered in amounts effective to produce a synergistic antineoplastic effect.

5. The method according to claim 3 wherein the mammal is a human.

6. A method of treating a mammal suffering from breast cancer, which method comprises administering to said mammal an acryloyl distamycin derivative, N-(5-{[(5-{[(5-{[(2-{[amino(imino)methyl]amino}ethyl)amino]carbonyl}-1-methyl-1H-pyrrol-3-yl)amino]carbonyl}-1-methyl-1H-pyrrol-3-yl)amino]carbonyl}-1-methyl-1H-pyrrol-3-yl)-4-[(2-bromoacryloyl)amino]-1-methyl-1H-pyrrole-2-carboxamide hydrochloride optionally in the form of a pharmaceutically acceptable salt, at a concentration of about 0.1 to about 50 mg/m$^2$ of body surface area;

and cisplatin at a concentration of about 10 to about 500 mg/m$^2$ of body surface area.

7. The method according to claim 6 wherein the mammal is a human.

* * * * *